United States Patent [19]

Kanno et al.

[11] Patent Number: 5,476,967
[45] Date of Patent: Dec. 19, 1995

[54] PRODUCTION METHOD OF ORGANIC SOLVENT SOLUTION OF DICHLOROGLYOXIME

[75] Inventors: Hideki Kanno; Hideki Yamamoto, both of Koshigaya, Japan

[73] Assignee: Junsei Chemical Co., Ltd., Tokyo, Japan

[21] Appl. No.: 281,023

[22] Filed: Jul. 27, 1994

[30] Foreign Application Priority Data

Jul. 27, 1993 [JP] Japan .................................. 5-185040

[51] Int. Cl.$^6$ ............................................. C07C 249/12
[52] U.S. Cl. .................................................... 564/268
[58] Field of Search ........................... 564/268; 514/640; 504/160, 344

[56] References Cited

U.S. PATENT DOCUMENTS 4,106,927  8/1978  Petree et al. .............................. 71/121
4,539,405  3/1985  Willer ...................................... 544/367

FOREIGN PATENT DOCUMENTS 21240    6/1971   Japan .
53201    3/1986   Japan .
22701    1/1987   Japan .
190602   7/1989   Japan .
316564   11/1992  Japan .
105604   4/1993   Japan .
1544767  2/1990   U.S.S.R. .
1307223  5/1970   United Kingdom .

OTHER PUBLICATIONS

Hsieh, et al., "Nitrogen–14 NQR Spectra of Glyoximes and Bis(glyoximato)–metal Complexes", Journal Of Magnetic Resonance21, 445–456 (1976).

Primary Examiner—Peter O'Sullivan
Attorney, Agent, or Firm—Sherman and Shalloway

[57] ABSTRACT

An organic solvent solution of glyoxime and a chlorinating agent are simultaneously charged into a reaction vessel to produce an organic solvent solution of dichloroglyoxime in a stable form, simply and in a high yield. Dichloroglyoxime is used as an industrial antibacterial agent, an antiseptic, a slime control agent, an agricultural chemical, and the like.

14 Claims, No Drawings

PRODUCTION METHOD OF ORGANIC SOLVENT SOLUTION OF DICHLOROGLYOXIME

FIELD OF THE INVENTION

This invention relates to a method for producing dichloroglyoxime, which is used as an industrial antibacterial agent, an antiseptic, a slime control agent, an agrochemical, and the like, in a safe form, simply, and in a high yield.

DESCRIPTION OF PRIOR ART

Heretofore, dichloroglyoxime has been used in industrial antibacterial agents, antiseptics, slime control agents, agricultural chemicals, and the like, normally in the form of a solution.

Dichloroglyoxime (III) has been known and produced for a long time, generally starting from glyoxal (I) to produce glyoxime (II), which is then chlorinated.

Production methods of glyoxime include, for example, the following.

(1) Reaction of aqueous glyoxal solution with hydroxylamine (W. V. Meyer, Chem. Ber., 16, 505 (1883); Ulpiani, Gazz. Chem. Ital., 42 I, 250 (1924); GB 1,307,223; U.S. Pat. No. 4,539,405)

(2) Reaction of dibromoacetaldehyde with hydroxylamine (Wittorf, Zh. Russ. Fiz.-Khim. O-va, 32, 97 (1900))

(3) Reaction of dichloroacetaldoxime with hydroxylamine (Routala, Neovius, Chem. Ber., 57, 253 (1924)).

Of these methods, the method (1) starting from aqueous glyoxal solution is the most preferable in view of raw material availability and economy.

Hydroxylamine to be reacted with glyoxal can be obtained by neutralizing a commercial inorganic acid salt of hydroxylamine, such as hydroxylamine sulfate or hydroxylamine hydrochloride, with an alkali.

In glyoxime synthesis, this neutralization is carried out in the presence of glyoxal, and precipitated glyoxime is filtered (GB 1,307,223; U.S. Pat. No. 4,539,405).

Another method uses free hydroxylamine. In this method, to an acid aqueous solution of glyoxal, a commercial 50% aqueous solution of hydroxylamine or an organic solvent solution of hydroxylamine, such as methanol, ethanol, propanol, or butanol solution, is added.

The above reactions are summarized as follows:

1. Oximization (1)

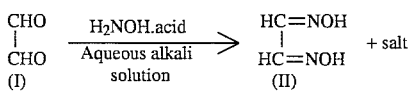

Oximization (2)

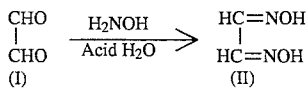

2. Chlorination

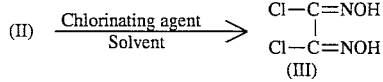

Some examples of dichloroglyoxime production methods are as follows:

(1) Reaction of α-glyoximecarboxylic acid with chlorine (Ponzio, de Paolini, Gazz. Chim. Ital., 56, 252 (1926))

(2) Reaction of furoxanecarboxylic acid with chlorine (Ponzio, de Paolini, Gazz. Chim. Ital., 56, 252 (1926))

(3) Reaction of glyoxime with chlorine in dilute hydrochloric acid (Ponzio, Gazz. Chim. Ital., 60, 434 (1930); Hauben, Kauffmann, Chem. Ber., 46, 2826 (1913); Steinkopf, Juergens, J. Prakt. Chem., <2>83, 467 (1911); B. G. White, GB 1,307,223)

(4) Reaction of glyoxime with chlorine in ethanol at −20° C. (Rodney L. Willer, U.S. Pat. No. 4,539,405).

In view of raw material availability and economy, the reaction of glyoxime with chlorine in the method (3) or (4) is preferable.

As a method for reacting glyoxime with chlorine, it is known that chlorine is blown into an aqueous suspension of glyoxime and hydrochloric acid, or an ethanol solution of glyoxime. In the former method, since dichloroglyoxime is obtained in the form of dilute hydrochloric acid suspension, it can be filtered and dried. In the latter method, after the reaction, ethanol is removed by vacuum distillation, and chloroform is added to obtain a slurry, which is filtered and dried. The latter method uses ethanol, but use of ethanol is not preferable because of its inflammability.

However, in these methods, glyoxime and dichloroglyoxime are handled in the form of crystals. The inventors have found that these compounds are very dangerous when handled in the form of crystals, because they are liable to cause explosion by mechanical shocks or friction. Therefore, these methods in which glyoxime and dichloroglyoxime are handled in the form of crystals should be dangerous methods.

Further, considering from the reaction method and yield, in the method of GB 1,307,223, chlorine is blown in 18 g of glyoxime and 70 ml of 10% HCl for 8 hours to yield 12 g (37.5%). In the method of Dirasat-Univ. Jordan, 13,1865-188 (1986), chlorine is blown at 0° C. into 5 g of glyoxime and 100 ml of 10% HCl to yield 3 g (33.5%). These methods are slow in reaction and thus give poor yields.

In the method of U.S. Pat. No. 4,539,405, chlorine is blown into a solution of 17.6 g of glyoxime and 200 ml of 95% ethanol at −20° C. for 30 minutes to yield 24.2 to 30.2 g (77 to 97%). This method is extremely low in yield unless the reaction is carried out at a low temperature of −20° C. for a short time. Through experiments conducted by the inventors, it has been found that when chlorine is blown at −20° C. for 5 hours, the yield is decreased to about 50%. When the reaction is carried out at 5° C. for 5 hours, the yield is further decreased to about 10%.

Chlorination of glyoxime is confirmed to have reaction steps shown in Formula 2.

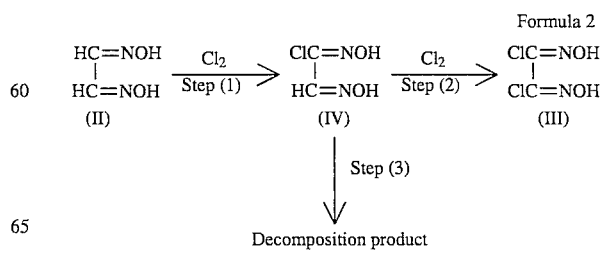

That is, it has been confirmed through a high-speed liquid chromatographic analysis of the reaction solution in the course of the reaction that the production process of dichloroglyoxime (III) (hereinafter referred to as DCG) shown in Formula 2 includes monochloroglyoxime (IV) (hereinafter referred to as MCG) as an intermediate. The intermediate MCG (IV) gradually decomposes even at a low temperature, and rapidly decomposes at higher temperatures, resulting in a reduction in the yield.

The inventors have found that a high concentration of chlorine causes the reaction to advance in the direction of step (2), rather than through step (3) to the decomposition product. However, the known method to blow chlorine into the glyoxime reaction solution has not a chlorine concentration sufficient to direct the resulting MCG immediately to DCG, the blown chlorine is preferentially spent for monochlorination of glyoxime in step (1). The MCG gradually decomposes even at a low temperature, and rapidly at higher temperatures. When the reaction for producing DCG begins in step (2), the raw material MCG is already exhausted by the decomposition, resulting in a considerably reduced yield of DCG.

Therefore, it has been found that, to obtain DCG in a high yield, 1 mole of glyoxime must be mixed with stoichiometrically 2 mole or more of chlorine at a time, so that easily decomposable MCG is immediately converted to stable DCG. In a large-scale production, in view of the chlorine supply capacity and the cooling capacity to remove the reaction heat, the experimental method of U.S. Pat. No. 4,539,405, in which chlorine is blown in a short time into an ethanol solution of glyoxime while maintaining a temperature of −20° C., is impossible to obtain the high yield as described.

The inventors have conducted intensive studies to find a method for producing dichloroglyoxime, which is used as an industrial antibacterial agent, an antiseptic, a slime control agent, an agricultural chemical, and the like, in a safe form, simply and in a high yield. Therefore, a primary object of the present invention is to provide a method for producing an organic solvent solution of dichloroglyoxime, safely, simply, and in a high yield.

SUMMARY OF THE INVENTION

In accordance with the present invention, there is provided a method for producing an organic solvent solution of dichloroglyoxime, characterized in that an organic solvent solution of glyoxime and a chlorinating agent are simultaneously charged into a reaction vessel. The organic solvent solution of glyoxime is preferably produced by a method in which an aqueous glyoxime solution obtained by reacting an aqueous glyoxal solution with an inorganic acid salt or organic acid salt of hydroxylamine and alkali is mixed with an organic solvent having a higher boiling point than water, or an organic solvent making an azeotrope with water, water is removed by distillation or azeotropic distillation, and precipitated salt is removed by filtration, or by a method in which a glyoxime reaction solution, obtained by reacting an aqueous glyoxal solution with free hydroxylamine in an acid medium, is mixed with an organic solvent having a higher boiling point than water, or an organic solvent making an azeotrope with water, or both, and water is removed by distillation or azeotropic distillation. The chlorinating agent is preferably chlorine or sulfuryl chloride.

That is, in the present invention, an aqueous glyoxal solution is oximized in an organic solvent to obtain a glyoxime reaction solution, which is chlorinated to obtain an organic solvent solution of dichloroglyoxime. Since raw materials and the product are not handled in the form of crystals, there is no danger of explosion due to mechanical shocks or friction. Therefore, the reaction is very safe, and the oximization and chlorination steps are continuously carried out in the solution state. Further, glyoxime and the chlorinating agent are simultaneously supplied to enhance the yield, with a simple method.

Then, the present invention will be described in detail.

Preferable oximization in the present invention will be described. Of the two raw materials, glyoxal and hydroxylamine, commercial glyoxal is generally supplied in the form of 40% aqueous solution. On the other hand, hydroxylamine includes use of an inorganic acid salt such as commercial hydroxylamine hydrochloride or sulfate, and use of free hydroxylamine.

When a commercial inorganic acid salt of hydroxylamine is used, it is used by neutralizing with alkali to prepare a free aqueous hydroxylamine solution. This neutralization is performed simultaneously with the oximization reaction. Specifically, the oximization reaction is carried out while adding an aqueous solution or solid of alkali, such as sodium hydroxide, potassium hydroxide, sodium carbonate, potassium carbonate, or the like, to aqueous hydroxylamine inorganic acid salt solution and 40% aqueous glyoxal solution. In this reaction, for efficient stirring, it is preferable to add a low-boiling solvent such as methanol, ethanol, or acetonitrile, in place of water, to facilitate water removal. After the reaction, glyoxime is obtained in the form of an aqueous suspension solution, in which some of glyoxime is dissolved.

In the known method using water as a solvent, after the reaction, the reaction solution is filtered to separate a solid, which is washed and dried to obtain a glyoxime crystal. However, this crystal has a danger of explosion by mechanical shocks or friction. Further, the filtrate irreversibly contains some of the objective glyoxime with inorganic salts, which reduces the yield. Extraction with an organic solvent is considered as a separation method of glyoxime, however, it has been found that a water-insoluble organic solvent, such as benzene, toluene, chloroform, ethyl acetate, ether, or the like, cannot efficiently extract glyoxime from the aqueous suspension solution.

Then, in the present invention, at least one organic solvent having a boiling point higher than water or making an azeotrope with water is added as an oximization solvent before or after the reaction, and water is removed by distillation or azeotropic distillation to obtain an organic solvent solution of glyoxime. In this method, to prevent decomposition of glyoxime, which is in general thermally unstable, it is preferable to distill at a low temperature under a reduced pressure. The suspension mixture of glyoxime organic solvent solution and precipitated inorganic salt obtained by removing water is then filtered to remove the inorganic salt, to obtain an organic solvent solution of glyoxime.

In the method using free hydroxylamine, a commercial 50% aqueous hydroxylamine solution (Nisshin Kako, FH-50) is mixed with 40% glyoxal in an acid medium for polymerization inhibition to obtain a glyoxime reaction solution. The solution is mixed with an organic solvent, which is the same as that used when an inorganic salt is used, before or after the reaction, then water is removed by distillation as in the use of the inorganic salt to obtain an organic solvent solution of glyoxime.

The organic solvent used in the method includes the following.

Ethylene glycol type: $RO-(CH_2CH_2O)_n-R^1$, wherein $R$, $R^1$ are H, Me, Et, Pr, Bu, or $CH_3CO$, and n is an integer from 1 to 10.

Examples of the ethylene glycol type solvent include ethylene glycol, diethylene glycol, triethylene glycol, polyethylene glycol, 2-methoxyethanol, 2-ethoxyethanol, 2-methoxyethyl acetate, 2-ethoxyethyl acetate, diethylene glycol monomethyl ether, diethylene glycol monoethyl ether, diethylene glycol dimethyl ether, diethylene glycol diethyl ether, diethylene glycol monomethyl ether acetate, and diethylene glycol monoethyl ether acetate.

Propylene glycol type: $R^2O-(CH(CH_3)CH_2O)_n'-R^3$, wherein R, $R^2$, $R^3$ are H, Me, Et, Pr, Bu, or $CH_3CO$, and n' is an integer from 1 to 10.

Examples of the propylene glycol type solvent include propylene glycol, dipropylene glycol, tripropylene glycol, polypropylene glycol, 2-methoxypropanol, 2-ethoxypropanol, 2-methoxypropyl acetate, 2-ethoxypropyl acetate, dipropylene glycol monomethyl ether, dipropylene glycol monoethyl ether, dipropylene glycol dimethyl ether, dipropylene glycol diethyl ether, dipropylene glycol monomethyl ether acetate, and dipropylene glycol monoethyl ether acetate.

Alkanol type: $C_n"H_{2n"+1}OH$, wherein n" is an integer from 2 to 18.

Examples of the alkanol type solvent include ethanol, 1-propanol, 2-propanol, 1-butanol, 2-butanol, isobutanol, tert-butanol, heptanol, hexanol, heptanol, octanol, nonanol, decanol, and dodecanol.

Amide type: for example, N,N-dimethylformamide, and N,N-dimethylacetamide.

Ester type: for example, ethyl acetate, butyl acetate, methyl propionate, ethyl propionate, methyl butyrate, ethyl butyrate, and ethyl benzoate.

Azeotropic solvent: benzene, toluene, xylene, carbon tetrachloride, 1,2-dichloroethane, cyclohexane, anisole, and the like.

Of these solvents, diethylene glycol monomethyl ether, and diethylene glycol monoethyl ether are preferable.

The method is advantageous in that, since an organic solvent solution of glyoxime is produced, it is safe to explosion by mechanical shocks, and the produced glyoxime is not lost as a filtrate out of the reaction system as seen in the known method, thereby obtaining a high yield.

Then, preferable chlorination of the resulting organic solvent solution of glyoxime will be described. In the method according to the present invention, in a reaction vessel such as a tank equipped with an agitator and a cooling system, or pipe or tower, the organic solvent solution of glyoxime obtained by the above oximization and a chlorinating agent are simultaneously charged in a ratio of more than 1:2, depending on the cooling capacity. In this method, a molar ratio of more than 1:2 is maintained within a limited time, including intermittent charging of one or both materials. The charging molar ratio is preferably 1:2 to 1:4. The reaction temperature is 30° to −30° C., preferably +10° to −10° C.

DETAILED DESCRIPTION OF PREFERRED EMBODIMENTS

The present invention will be described further in detail with reference to the examples.

COMPARATIVE EXAMPLE 1

In a 3-liter four-necked flask, 580 g (4 mole) of 40% glyoxal, 556 g (8 mole) of hydroxylamine hydrochloride, and 150 ml of water were placed, 916 g (8 mole) of 35% aqueous sodium hydroxide solution was dropped at 10° to 20° C. under cooling. After allowing to stand overnight at room temperature, the mixture was heated to 100° C. to dissolve the precipitated crystal, and gradually cooled to 3° C. to recrystallize. The crystal was filtered, washed with 500 ml of cold water and dried in vacuo to obtain 29.4 g (yield: 83.5%) of white crystal. The melting point was 147° C. (dec.).

COMPARATIVE EXAMPLE 2

In a 1-liter four-necked flask, 35.2 g (0.4 mole) of glyoxime and 400 ml of ethanol were placed, cooled in a dry ice/methanol bath, and 70 g (0.984 mole) of chlorine was blown in at below −20° C. for 30 minutes. After elevating to room temperature, ethanol was distilled out under reduced pressure, 100 ml of chloroform was added to disperse the crystal, the crystal was filtered, and dried in vacuo to obtain 52.9 g (yield: 84.3%) of pale yellow crystal. The melting point was 204° C. The overall yield from glyoxal in Reference Example 1 is 70.4%.

COMPARATIVE EXAMPLE 3

In a 1-liter four-necked flask, 35.2 g (0.4 mole) of glyoxime and 400 ml of ethanol were placed, cooled in a dry ice/methanol bath, and 70 g (0.984 mole) of chlorine was blown in at below −20° C. for 5 hours. After elevating to room temperature, ethanol was distilled out under vacuum, 100 ml of chloroform was added to disperse the crystal, the crystal was filtered, and dried in vacuo to obtain 28.6 g (yield: 45.6%) of while crystal. The melting point was 202° C.

COMPARATIVE EXAMPLE 4

In a 1-liter four-necked flask, 1980 g of diethylene glycol monomethyl ether solution containing 172.1 g (1.95 mole) of glyoxime was placed, and 350 g (4.94 mole) of chlorine was blown in at about 15° C. for 4.5 hours. After removing HCl gas, the product solution weighed 2114 g. The DCG content, measured by HPLC and calculated by an absolute calibration curve method, was 1.54%, and thus the yield was 32.6 g (10.4%).

EXAMPLE 1

In a 300-liter glass lining reactor, 29 kg (200 mole) of 40% glyoxal, 0.35 kg of concentrated hydrochloric acid, and 50 kg of diethylene glycol monomethyl ether were charged, and 26.4 kg (400 mole) of 50% hydroxylamine was added dropwise at 20° C. After stirring overnight, water was removed under vacuum (internal temperature: 60° C.) to obtain 155 kg of brown diethylene glycol monomethyl ether solution of glyoxime.

In a 300-liter glass lining reactor, 95 kg of diethylene glycol monomethyl ether was charged, the above diethylene glycol monomethyl ether solution of glyoxime and chlorine were simultaneously added at below 5° C. so that the molar ratio of glyoxime and chlorine in the solution was 1:3. After reacting for 10 hours, hydrogen chloride was removed under vacuum to obtain 257 kg of pale yellow solution. The HPLC content was 11.0%, and thus the yield was 90.1%.

EXAMPLES 2

In a 3-liter four-necked flask, 328 g (2 mole) of hydroxylammonium sulfate, 290 g (2 mole) of 40% glyoxal, and 350 g of water were charged, 459 g (4 mole) of 35% aqueous sodium hydroxide solution was dropped under cooling at below 15° C. After stirring overnight, 1300 g of diethylene glycol monomethyl ether was added, and water was distilled out under vacuum (internal temperature: 60° C.). After cooling to 10° C., precipitated sodium sulfate crystal was filtered, the crystal was washed with 200 g of diethylene glycol monomethyl ether, and the filtrate and the washing solvent were combined to obtain 1473 g of brown diethylene glycol monomethyl ether solution of glyoxime.

In a 3-liter four-necked flask, 700 g of diethylene glycol monomethyl ether was charged, the above diethylene glycol monomethyl ether solution of glyoxime and chlorine were simultaneously added at below 5° C. so that the molar ratio of glyoxime and chlorine in the solution was 1:3. After the completion of the reaction, hydrogen chloride was removed under vacuum to obtain 2477 g of pale yellow solution. The HPLC content was 11.22%, and thus the yield was 88.5%.

EXAMPLE 3

In a 300-ml four-necked flask, 32.8 g (0.2 mole) of hydroxylammonium sulfate and 29.0 g (0.2 mole) of 40% glyoxal were charged, 45.9 g (0.4 mole) of 35% aqueous sodium hydroxide solution was dropped at below 10° C., and allowed to stand overnight. On the next day, 160 g of diethylene glycol monomethyl ether was added, and water was distilled out under vacuum by a rotary evaporator. Precipitated sodium sulfate crystal was filtered, the crystal on the filter paper was washed with 64 g of diethylene glycol monomethyl ether, and the filtrate and the washing solvent were combined. The combined diethylene glycol monomethyl ether solution of glyoxime was charged in a 500-ml four-necked flask, and 29 g (0.409 mole) of chlorine was blown in at below 5° C. for 30 minutes. After vacuum degassing, 260.5 g of nearly colorless solution was obtained. The dichloroglyoxime content, measured by HPLC and calculated by an absolute calibration curve method, was 11.2% and thus the yield was 93.0%.

EXAMPLES 4 to 15

Synthesis of dichloroglyoxime was carried out using the same procedure as in Example 3 but with different types of solvents, and yields were calculated from the weight of the resulting dichloroglyoxime organic solvent solution and the content calculated by the HPLC absolute calibration curve method. The solvents used and the yields are shown as Examples below.

| Example 4: | 2-Methoxyethanol | 82.6% |
| --- | --- | --- |
| Example 5: | Diethylene glycol | 84.9% |
| Example 6: | Methoxypolyethylene glycol | 83.5% |
| Example 7: | Ethylene glycol | 21.3% |
| Example 8: | Propylene glycol | 50.3% |
| Example 9: | Propylene glycol monomethyl ether | 94.3% |
| Example 10: | Diethylene glycol monomethyl ether acetate | 77.2% |
| Example 11: | Diethylene glycol dimethyl ether | 86.1% |
| Example 12: | Diethylene glycol diacetate | 91.1% |
| Example 13: | N,N-dimethylformamide | Overlapped with solvent peak |
| Example 14: | Butyl acetate | 78.3% |
| Example 15: | Ethyl benzoate | 66.4% |

EXAMPLE 16

In a 500-ml four-necked flask, 43 g (0.32 mole) of sulfuryl chloride was charged, 100 g of the diethylene glycol monomethyl ether solution of glyoxime obtained by the same method as in Example 2 (containing 11 g (0.125 mole) of glyoxime) and 167 g (1.24 mole) of sulfuryl chloride were added dropwise at the same rates under stirring at below 5° C. After the completion of the reaction, generated hydrogen chloride gas and sulfur dioxide gas were removed under vacuum, and further excess sulfuryl chloride was distilled out. The residue was diluted with diethylene glycol monomethyl ether to obtain 360 g of solution. The dichloroglyoxime content, measured by HPLC, was 1.49%. The net yield was 5.4 g, and thus the yield was 27.4%.

In the present invention, in producing an organic solvent solution of dichloroglyoxime, which has a very high antibacterial activity, chlorination of glyoxime organic solvent solution is carried out in a condition where more than 2 moles of chlorine is present based on 1 mole of glyoxime to obtain an organic solvent solution of dichloroglyoxime in a high yield. In particular, when dichloroglyoxime is produced from glyoxal in an organic solvent solution in a start-to-finish production line, since the explosive intermediate glyoxime and dichloroglyoxime are present in the form of solutions, production can be conducted safely, is advantageous because the reaction solvent is also used as the final solvent, and the production does not emit large amounts of waste liquid, thereby achieving a high yield by a simple process.

We claim:

1. A method for producing an organic solvent solution of dichloroglyoxime, said method comprising simultaneously charging an organic solvent solution of glyoxime and a chlorinating agent into a reaction vessel to react at a temperature of −30° C. to +30° C., wherein said organic solvent solution of glyoxime and said chlorinating agent are fed to said reaction vessel such that 2 moles or more of said chlorinating agent are supplied to each mole of glyoxime, wherein said chlorinating agent is chlorine or sulfuryl chloride.

2. The method of claim 1, wherein the molar ratio of glyoxime to said chlorinating agent is 1:2 to 1:4.

3. The method of claim 1, wherein said organic solvent solution of glyoxime is produced by the method comprising reacting an aqueous glyoxal solution with an inorganic acid salt of hydroxylamine and an aqueous alkali solution to form a reaction mixture;

mixing an organic solvent with said reaction mixture, said organic solvent having a higher boiling point than water and/or forming an azeotrope with water;

removing water from said mixture by distillation or azeotropic distillation; and removing precipitated salts from said mixture by filtration.

4. The method of claim 3, wherein said inorganic acid salt of hydroxylamine is hydroxylamine hydrochloride or hydroxylamine sulfate.

5. The method of claim 1, wherein said organic solvent solution of glyoxime is produced by the method comprising reacting an aqueous glyoxal solution with a free hydroxyl amine in an acid medium to form a reaction mixture;

mixture an organic solvent with said reaction mixture, said organic solvent having a higher boiling point than water and/or forming an azeotrope with water;

removing water from said mixture by distillation or azeotropic distillation.

6. The method of claim 5, wherein said free hydroxylamine is an aqueous solution of hydroxylamine, an ethanol solution of hydroxylamine, a propanol solution of hydroylamine or a butanol solution of hydroxylamine.

7. The method of claim 1, wherein said organic solvent is selected from the group consisting of ethylene glycol-based solvents of the formula RO$-(CH_2CH_2O)_n-R^1$ wherein R and $R^1$ are independently hydrogen, methyl, ethyl, propyl, butyl or $CH_3CO$ and n is an integer of 1 to 10; propylene glycol-based solvents of the formula $R^2O-(CH(CH_3)CH_2O)_m-R^3$ wherein $R^2$ and $R^3$ are independently hydrogen, methyl, ethyl, propyl, butyl or $CH_3CO$ and m is an integer of 1 to 10; alkanol-based solvents of the formula $C_lH_{2l+1}OH$ wherein l is an integer of 2 to 18; amides; esters; and solvents making an azeotrope with water.

8. The method of claim 7, wherein said ethylene glycol-based solvents are selected from the group consisting of ethylene glycol, diethylene glycol, triethylene glycol, polyethylene glycol, 2-methoxethanol, 2-ethoxyethanol, 2-methoxyethyl acetate, 2-ethoxyethyl acetate, diethylene glycol monomethyl ether, diethylene glycol monoethyl ether, diethylene glycol dimethyl ether, diethylene glycol diethyl ether, diethylene glycol monomethyl ether acetate, and diethylene glycol monoethyl ether acetate.

9. The method of claim 7, wherein said propylene glycol-based solvents are selected from the group consisting of propylene glycol, dipropylene glycol, tripropylene glycol, polypropylene glycol, 2-methoxypropanol, 2-ethoxypropanol, 2-methoxypropyl acetate, 2 ethoxypropyl acetate, dipropylene glycol monomethyl ether, dipropylene glycol monoethyl ether, dipropylene glycol monomethyl ether acetate, and dipropylene glycol monoethyl ether acetate.

10. The method of claim 7, wherein said alkanol-based solvents are selected from the group consisting of ethanol, 1-propanol, 2-propanol, 1-butanol, 2-butanol, isobutanol, tert-butanol, pentanol, hexanol, heptanol, octanol, nonanol, decanol, and dodecanol.

11. The method of claim 7, wherein the amide solvents are selected from the group consisting of N,N-dimethylformamide and N,N-diemthylacetamide.

12. The method of claim 7, wherein the ester solvents are selected from the group consisting of ethyl acetate, butyl acetate, methyl propionate, ethyl propionate, methyl butyrate, ethyl butyrate, and ethyl benzoate.

13. The method of claim 7, wherein said solvents making an azeotrope with water are selected from the group consisting of benzene, toluene, xylene, carbon tetrachloride, 1,2-dichloro-ethane, cyclohexane, and anisole.

14. The method of claim 7, wherein said organic solvent is diethylene glycol monomethyl ether or diethylene glycol monoethyl ether.

* * * * *